United States Patent [19]

Yokoyama et al.

[11] 4,252,827
[45] Feb. 24, 1981

[54] OXYGEN-TRANSFERABLE FLUOROCARBON EMULSION

[75] Inventors: Kazumasa Yokoyama, Suita; Kouichi Yamanouchi, Sakai; Ryoichiro Murashima, Kashihara; Yoshio Tsuda, Kyoto, all of Japan

[73] Assignee: The Green Cross Corporation, Osaka, Japan

[21] Appl. No.: 41,794

[22] Filed: May 23, 1979

Related U.S. Application Data

[63] Continuation of Ser. No. 654,964, Feb. 3, 1976, abandoned.

[51] Int. Cl.$^3$ .............................................. A61K 45/00
[52] U.S. Cl. ........................................................ 424/366
[58] Field of Search ................................. 424/366, 352

[56] References Cited

U.S. PATENT DOCUMENTS 3,911,138  10/1975  Clark ...................................... 424/352
3,962,439   6/1976  Yokoyama et al. ................... 424/352

*Primary Examiner*—Frederick E. Waddell
*Attorney, Agent, or Firm*—Cushman, Darby & Cushman

[57] ABSTRACT

50–95 Parts by weight of a perfluorocarbon compound such as perfluorodecalin, perfluoromethyldecalin, perfluoro alkylcyclohexanes having 3 to 5 carbon atoms in the alkyl, perfluoro alkyltetrahydrofurans having 5 to 7 carbon atoms in the alkyl, perfluoro alkyltetrahydropyrans having 4 to 6 carbon atoms in the alkyl, perfluoroalkanes having 9 to 11 carbon atoms, and 50–5 parts by weight of a perfluoro tert.-amine such as perfluoro tert.-alkylamines having 9–11 carbon atoms, perfluoro N-alkylpiperidines having 4 to 6 carbon atoms in the alkyl, and perfluoro N-alkylmorpholines having 5 to 7 carbon atoms in the alkyl are emulsified in an aqueous medium by the aid of a high-molecular-weight nonionic surfactant have a molecular weight of about 2,000 to 20,000, and phospholipids as emulsifying agent, and fatty acids having 8 to 22 carbon atoms or salts or monoglycerides thereof as emulsifying adjuvant.

The resulting oxygen-transferable emulsion having a particle size of 0.05 to 0.25$\mu$ is very stable for a long period of time, can be mixed with plasma extenders, and retains for long time in the blood stream of animals when it is used as an artificial blood substitute while being excreted very rapidly.

20 Claims, No Drawings

OXYGEN-TRANSFERABLE FLUOROCARBON EMULSION

This is a continuation, of application Ser. No. 654,964 filed Feb. 3, 1976, now abandoned.

This invention relates to an oxygen-transferable fluorocarbon compound emulsion for injection and perfusion, which is used in the lifesaving of a patient suffering from massive hemorrhage and in the preservation of internal organs in transplantation.

It has already been reported by a number of research people that fluorocarbon compound emulsions may possibly be used as an artificial blood substitute for mammals and as a perfusion fluid for preservation of internal organs to be transplated, particularly as a substitute infusion fluid capable of transporting oxygen [Leland C. Clark, Jr., F. Becattini, and S. Kaplan: The physiology of synthetic blood., Journal of Thoracic Cardiovascular Surgery, 60, 757–773 (1970); R. P. Geyer: Fluorocarbon-polyol artificial blood substitutes, New England Journal of Medicine, 289, 1077–1082 (1973)].

These emulsions, however, cannot be assumed as satisfactory enough for practical use, in view of their pharmaceutical stability and of safety of living animal body. In order that fluorocarbon compound emulsions be qualified for practical use as an artificial blood substitute, it is necessary to develop a preparation which is sufficiently stable to be kept for a long period of time without change in particle size.

In fluorocarbon compound emulsions, the size of particle plays an important role in the toxicity and efficacy of the emulsion [K. Yokoyama, K. Yamanouchi, M. Watanabe, R. Murashima, T. Matsumoto, T. Hamano, H. Okamoto, T. Suyama, R. Watanabe, and R. Naitoh: Preparation of perfluorodecalin emulsion, an approach to the red cells substitute., Federation Proceeding, 34, 1478–1483 (May, 1975)]. An emulsion of larger particle size is more toxic and shorter in retention time of the particles in the blood stream. Accordingly, when the fluorocarbon compound emulsion is intended for use as an artificial blood substitute for saving the life of a patient suffering from massive hemorrhage, its average particle size should be $0.3\mu$ or less in diameter, preferably $0.2\mu$ or less [Japanese Patent Application Kokai (Laid Open) No. 22612/73].

Besides the particle size, in order that the fluorocarbon compound emulsion be usable as artificial blood substitute, it is necessary that after being eliminated from the blood stream, the intravenously administered fluorocarbon compound must be excreted from the body as rapidly as possible. Some of the present inventors had previously studied on the excretion rate and toxicity of several sorts of fluorocarbon compound emulsions and, as a result, found that perfluorocarbon compounds of 9 to 11 carbon atoms are usable as the material of artificial blood substitute, particularly perfluorodecalin being the best of all [K. Yokoyama, K. Yamanouchi, and R. Murashima: Excretion of perfluorochemicals after intravenous injection of their emulsion., Chemical Pharmaceutical Bulletin, 23, 1368–1373 (June, 1975)].

In addition, some of the present inventors had also found that the fine and stable fluorocarbon compound emulsion can be prepared from these selected fluorocarbon compounds of 9 to 11 carbon atoms by emulsifying said fluorocarbon compounds with the mixture of egg yolk phospholipids or soybean phospholipids and a small amount of fatty acids of 8 to 22 carbon atoms or salts thereof or monoglycerides thereof [Japanese Patent Application Kokai (Laid Open), No. 69,219/75 corresponding to U.S. Pat. No. 3,962,439].

However, compared with a perfluorotributylamine emulsion stabilized with a high-molecular-weight polyoxyethylene-polyoxypropylene copolymer emulsifier (R. P. Geyer, loc. cit.), the above-noted emulsion stabilized with both phospholipids and fatty acids is superior in the rate of excretion, but inferior in the stability in circulating blood stream after intravenous injection, the half life being about two-thirds of that of the former.

Further, a fluorocarbon compound emulsion prepared with a high-molecular-weight nonionic surface active agent such as perfluorotributylamine emulsion, can be used as a mixture of any proportion with the commercial plasma expanders such as dextran, or hydroxyethylstarch, or modified gelatin solution, whereas the perfluorodecalin emulsion described in Japanese Patent Application Kokai (Laid Open) No. 69,219/75 corresponding to U.S. Pat. No. 3,962,439 cannot be used in combination with said plasma expander because of formation of precipitates when mixed with the latter. It seems that the precipitation is due to the destruction of emulsified particles caused by interaction between the phospholipids contained in a high concentration in the emulsion and the plasma expander, such as dextran or hydroxyethylstarch, which is a high-molecular-weight colloidal substance.

When it is intended to use a fluorocarbon compound emulsion as an infusion fluid or an artificial blood substitute to save the life of patient in the case of massive hemorrhage, the combined used with a plasma expander becomes important in order to make isotonicity, that is, to equalize oncotic pressures of both colloidal solutions, i.e. the emulsion and the blood; the fluorocarbon compound emulsion supplies oxygen, while the plasma expander makes it possible to maintain the circulating blood volume at a proper level. Therefore, it is preferable to use a high-molecular-weight nonionic surface active agent which is inactive with the plasma expnader, in preparing a fluorocarbon emulsion intended for use as an artificial blood. Although these high-molecular-weight nonionic surface active agents are effective for some fluorocarbon compounds such as perfluorotributylamine and other amine-type fluorocarbons as an emulsifier, they are not suitable for fluorocarbon compounds of 9 to 11 carbon atoms, such as perfluorodecalin, which have a high rate of excretion.

Under the circumstances, the present inventors conducted extensive pharmaceutical investigations on preparing the emulsions of those fluorocarbons of 9 to 11 carbon atoms represented by perfluorodecalin, which have a high rate of excretion, which emulsions are stable in the circulating blood stream and are able to mix with the plasma expander without any destruction of emulsified particles. As a result, the present invention has now been accomplished.

According to this invention, there is provided a stable emulsion in a physiologically acceptable aqueous medium of an oxygen-transferable perfluorocarbon compound having a particle size of about 0.05 to $0.3\mu$, which comprises (A) at least one perfluorocarbon compound having 9–11 carbon atoms selected from the group consisting of perfluorodecalin, perfluoromethyldecalin, perfluoro alkylcyclohexanes having 3 to 5 carbon atoms in the alkyl, perfluoro alkyltetrahydrofurans having 5 to 7 carbon atoms in the alkyl, perfluoro alkyl-tetrahydropyrans having 4 to 6 carbon atoms in the alkyl, perfluoroalkanes having 9 to 11 carbon atoms; (B) at least one perfluoro tert-amine having 9 to 11 carbon atoms selected from the group consisting of perfluoro tert-alkylamines having 9 to 11 carbon atoms, perfluoro N-alkylpiperidines having 4 to 6 carbon atoms in the alkyl, and perfluoro N-alkylmorpholines having 5 to 7 carbon atoms in the alkyl; a high-molecular-weight nonionic surfactant having a molecular weight of about 2,000 to 20,000; a phospholipid; and at least one fatty acid compound selected from the group consisting of fatty acids having 8 to 22 carbon atoms, physiologically acceptable salts and monoglycerides thereof; the ratio of the said perfluorocarbon compound and the said perfluoro-tert-amine being 95–50 to 5–50 by weight.

The "high-molecular-weight nonionic surfactant", as herein referred to, has a molecular weight of 2,000 to 20,000 and includes polyoxyethylene-polyoxypropylene copolymers, polyoxyethylene alkyl ethers, and polyoxyethylene alkyl aryl ethers. The concentration of said surfactant in the emulsion is about 2.0 to about 5.0, preferably 3.0 to 3.5, % (W/V).

The symbol "% (W/V)" referred to in the specification and claim of this application means the amount proportion of a material by weight (gram) based on 100 ml of the resulting emulsion.

Examples of the perfluorocarbons (A) having 9 to 11 carbon atoms are a perfluorocycloalkane or perfluoro alkylcycloalkane which includes, for example, perfluoro $C_{3-5}$-alkylcyclohexanes such as perfluoromethylpropylcyclohexane, perfluorobutylcyclohexane, perfluorotrimethylcyclohexane, perfluoroethylpropylcyclohexane, perfluorodecalin and perfluoromethyldecalin; a perfluoro $C_{4-6}$-alkyltetrahydropyran such as perfluorohexyltetrahydropyran; a perfluoro $C_{5-7}$-alkyltetrahydrofuran such as perfluoro pentyltetrahydrofuran, perfluoro hexyltetrahydrofuran and perfluoro heptyltetrahydrofuran; and a perfluoroalkane having 9–11 carbon atoms such as perfluorononane and perfluorodecane.

Examples of the perfluoro tert-amine (B) having 9 to 11 carbon atoms are a perfluoro tert-alkylamine having 9 to 11 carbon atoms which includes, for example, perfluorotrialkylamines such as perfluoro N,N-dibutylmonomethylamine, perfluoro N,N-diethylpentylamine, perfluoro N,N-diethylhexylamine, perfluoro N,N-dipropylbutylamine and perfluorotripropylamine; a perfluoro N,N-dialkylcyclohexylamine having 9–11 carbon atoms such as perfluoro N,N-diethylcyclohexylamine; a perfluoro N-$C_{4-6}$-alkylpiperidine such as perfluoro N-pentylpiperidine, perfluoro N-hexylpiperidine and perfluoro N-butylpiperidine; and a perfluoro N-$C_{5-7}$-alkylmorpholine such as perfluoro N-pentylmorpholine, perfluoro N-hexylmorpholine and perfluoro N-heptylmorpholine.

The ratio of the perfluorocarbon compound (A) to the perfluoro tert-amine (B) to be used is 50–95 to 50–5 by weight and the total amount of (A) and (B) contained in the emulsion is about 10 to about 50% (W/V).

The phospholipids used as emulsifier adjuvant in the invention are ones commonly used in the art, and those comprising yolk phospholipid or soybean phospholipid are preferable. The amount present in the emulsion ranges from about 0.1 to about 1.0% (W/V), and preferably about 0.4 to about 0.6% (W/V).

The fatty acid compound used as emulsifying adjuvant is a fatty acid having 8 to 22 carbon atoms, a physiologically acceptable salt such as sodium or potassium salt or a monoglyceride thereof, which includes, for example, caprylic acid, capric acid, lauric acid, myristic acid, palmitic acid, stearic acid, behenic acid, palmitoleic acid, oleic acid, linoleic acid, arachidonic acid and sodium or potassium salt and monoglyceride thereof. These fatty acid compounds may be used alone or as a mixture of two or more kinds thereof in such a minor amount of 0.004 to 0.1% (W/V), and preferably about 0.02 to 0.04% (W/V). Among these fatty acid compounds, the preferable ones are those having 14 to 20 carbon atoms and their physiologically acceptable salts, and the most preferable are potassium palmitate and potassium oleate, taking into consideration of their good solubility and ease of the preparation of the emulsion.

The fluorocarbon compound emulsion of this invention is prepared by mixing prescribed amounts of the aforesaid components in any order in a physiologically acceptable aqueous medium, such as distilled water, to obtain a crude emulsion, and then emulsifying the crude emulsion by means of an effective emulsifier until the average particle diameter becomes 0.05 to 0.25μ.

The emulsification is attained by means of a high pressure homogenizer, which is a high pressure pump which homogenizes a mixture of two immiscible liquids by injecting through a slit under a high pressure at a very high velocity to give a shear and mixing to the liquids. The typical homogenizer on market is Manton-Gaulic type homogenizer (Trade Mark of this type of homogenizer sold by Manton-Gaulin Manufacturing Co., In., U.S.A.) which has a multiple-stage valve in combination of two or more valves each having a spring therein by which the slits are formed.

The mixture is circulated in this type of homogenizer several times under the total pressure of about 500 kg/cm$^2$ thereby to obtain the stable emulsion of the invention. The operating temperature is kept in a range of up to 55° C., and preferably 25° to 40° C.

The present emulsion has a dispersed phase of ultra-fine particles whose diameter is less than 0.2μ or at most less than 0.3μ. Moreover, it is stable, showing no growth in particle size, even when heated or stored for a long period of time. Therefore, the present emulsion thus secures the administered animal to a high degree against harmful effect due to agglomeration of the emulsion particles.

The present emulsion, however, has a long retention time in the circulating blood stream, so that the oxygen-carrying capacity is maintained for a long period.

For instance, as compared with a fluorocarbon compound emulsion prepared by use of phospholipids as emulsifier according to Japanese Patent Application Kokai (Laid Open) No. 69219/75, corresponding to U.S. Pat. No. 3,962,439 the present emulsion retains for much longer time in the blood stream of animal. The excretion of the present emulsion from the body is far faster than that of a perfluorotributylamine emulsion.

The present emulsion may be used as infusion fluid, after having been made physiologically isotonic. It may be used also as mixtures with commercial plasma expanders such as Dextran, hydroxyethylstarch, and modified gelatin. Further, it can be used as a blood substitute for mammals and as a perfusate for preserving internal organs.

The present invention is further illustrated by the following Examples which should not be construed to limit the invention thereto.

In Examples the particle size was measured by the centrifugal sedimentation method proposed by K. Yokoyama, A. Suzuki, I. Utsumi and R. Naito. (Chem. Pharm. Bull. 22 (12), 2966–2971 (1974))

EXAMPLE 1

In 8 liters of distilled water, was dissolved 300 g of a polyoxyethylene-polyoxypropylene copolymer (molecular weight: 10,800). To the solution were added 40 g of soybean phospholipids, 2 g of potassium oleate, and a mixture comprising 3 kg of perfluorodecalin and 300 g of perfluorotripropylamine. The resulting mixture was stirred in a mixer to form a crude emulsion. The resulting crude emulsion was charged into the liquor tank of a jet emulsifier (made by Manton-Gaulin Co.) and emulsified by passing it twelve times through a valve at a high pressure of 200 to 500 kg/cm$^2$, while maintaining the liquor temperature at 35°±5° C., to effect emulsification. The resulting emulsion contained 30.5% (W/V) of perfluorodecalin and 2.9% (W/V) of perfluorotripropylamine. The average particle diameter was 0.09 to 0.1μ, as measured by the centrifugal sedimentation method. The emulsion showed substantially no growth in particle size, when enclosed in a vial for injection and subjected to thermal sterilization at 115° C. for 12 minutes in the special designed rotary sterilizer. In Table 1 are shown the particle size distribution of this emulsion and that of an emulsion of perfluorodecalin alone prepared without using perfluorotripropylamine.

As seen from Table 1, when stored at 4° C. for 6 months, the present emulsion did not show any agglomeration, the mean particle diameter having been substantially unchanged.

The above procedure was repeated, except that perfluoropentyltetrahydrofuran was used in place of the perfluorodecalin, and similar results to those shown above were obtained.

EXAMPLE 2

In 8 liters of distilled water, was dissolved 330 g of a polyoxyethylene octyl ether (average molecular weight: 3,500). To the solution were added 40 g of soybean phospholipid and 2 g of potassium oleate, and the resulting mixture was stirred in a mixer to prepare a dispersion. To the dispersion was added a mixture comprising 3 kg of perfluoromethyldecalin and 600 g of perfluoro-N-pentylpiperidine and the resulting mixture was stirred in a mixer to prepare a crude emulsion. The crude emulsion was thoroughly emulsified in the same manner as in Example 1, and the resulting emulsion was filled in small vials. The vial containing the emulsion was subjected to thermal sterilization at 115° C. for 12 minutes in the rotary sterilizer. The emulsion contained 29.7% (W/V) of perfluoromethyldecalin and 5.8% (W/V) of perfluoro-N-pentylpiperidine. The particle size distribution after sterilization and the average particle diameter after storage at 4° C. for 6 months, as well as those of a reference emulsion of perfluorodecalin alone were as shown in Table 1.

EXAMPLE 3

In 2 liters of distilled water, was dissolved 100 g of a polyoxyethylene-polyoxypropylene having an average molecular weight of 8,350. To the resulting solution were added 20 g of yolk phospholipids and 0.5 g of oleic acid, and the mixture was stirred in a mixer to prepare a dispersion. To the dispersion was added a mixture comprising 640 g of perfluorodecalin and 250 g of perfluorodibutylmonomethylamine, and the resulting mixture was stirred in a mixer to obtain a crude emulsion. The crude emulsion was emulsified in the same manner as in Example 1 and sterilized by heating at 115° C. for 12 min. in the rotary sterilizer. The emulsion contained 25.3% (W/V) of perfluorodecalin and 9.8% (W/V) of perfluorodibutylmonomethylamine. The average particle diameter and the particle size distribution of the present emulsion and those of a reference sample of an emulsion prepared by use of perfluorodecalin alone were as shown in Table 1. In Table 1 is also shown the average particle diameter of the present emulsion after storage at 4° C. for 6 months.

EXAMPLE 4

In 800 ml of distilled water, was dissolved 35 g of a polyoxyethylene-polyoxypropylene copolymer having an average molecular weight of 15,800. To the solution were added 4 g of yolk phospholipids and 0.1 g of monoglyceride of lauric acid, and the resulting mixture was stirred in a mixer to prepare a dispersion. To the dispersion was added a mixture comprising 350 g of perfluorohexyltetrahydropyran and 40 g of perfluoro-N,N-diethylcyclohexylamine, and the resulting mixture was stirred in a mixer to prepare a crude emulsion. The crude emulsion was further emulsified in the same manner as in Example 1, and the resulting emulsion was subdivided into small portions which were enclosed in vials. The vial containing the emulsion was subjected to thermal sterilization at 115° C. for 12 min. in a rotary sterilizer. The emulsion contained 35.7% (W/V) of perfluorohexyltetrahydropyran and 4.1% (W/V) of perfluoro-N,N-diethylcyclohexylamine.

The average particle diameter of the present emulsion and that of a reference sample of emulsion prepared by use of perfluorohyxyltetrahydropyran alone after sterilization is shown in Table 1. The present emulsion showed no change of particle size after storage at 4° C. for 6 months.

TABLE 1

Particle size distribution of various emulsions

| Example No. | (A) Fluorocarbon compound, % (W/V) | | (B) Perfluoro-tert-amine, % (W/V) | | Emulsifier, % (W/V) | | Emulsifying adjuvant, % (W/V) | | Average particle diameter, μ | | Particle size distribution after sterilization, % by wt. Particle diameter | | | |
|---|---|---|---|---|---|---|---|---|---|---|---|---|---|---|
| | | | | | | | | | After sterilization | After storage (4° C., 6 mo.) | <0.1μ | 0.1-0.2μ | 0.2-0.3μ | >0.3μ |
| 1 | Perfluoro-decalin | 30.5 | Perfluorotripropylamine | 2.9 | A$_1$* | 3.0 | Soybean phospholipids K oleate | 0.4 0.02 | 0.097 | 0.099 | 58.3 | 39.1 | 2.6 | 0 |
| | | 30 | — | | A$_1$* | 3.0 | Soybean phospholipids K oleate | 0.4 0.02 | 0.395 | >0.4 | 3.9 | 11.7 | 24.1 | 60.3 |
| 2 | Perfluoro-methyldecalin | 29.7 | Perfluoro-N-pentyl-piperidine | 5.8 | B* | 3.3 | Soybean phospholipids K oleate | 0.4 0.002 | 0.088 | 0.090 | 63.6 | 35.9 | 0.5 | 0 |
| | | 30 | — | | B* | 3.3 | Soybean phospholipids K oleate | 0.4 0.02 | 0.273 | >0.4 | 10.6 | 20.5 | 42.0 | 26.9 |
| 3 | Perfluoro-decalin | 25.3 | Perfluorodibutyl-monomethylamine | 9.8 | A$_2$* | 4.0 | Egg yolk phospholipids Oleic acid | 0.8 0.02 | 0.090 | 0.091 | 61.9 | 37.2 | 0.9 | 0 |
| | | 25 | — | | A$_2$* | 4.0 | Egg yolk phospholipids Oleic acid | 0.8 0.02 | 0.245 | >0.4 | 11.9 | 18.7 | 46.4 | 23.0 |
| 4 | Perfluoro-hexyl-tetrahydro-pyran | 35.7 | Perfluoro-N,N-diethyl-cyclohexylamine | | A$_3$* | 3.5 | Egg yolk phospholipids Lauric acid monoglyceride | 0.4 0.01 | 0.102 | 0.112 | 49.0 | 43.2 | 7.8 | 0 |
| | | 35 | — | 4.1 | A$_3$* | 3.5 | Egg yolk phospholipids Lauric acid monoglyceride | 0.4 0.01 | 0.298 | >0.4 | 9.3 | 18.6 | 25.4 | 46.7 |

Note:
*A: Polyoxyethylene-polyoxypropylene copolymer. Average molecular weight: A$_1$ 10,800; A$_2$ 8,350; A$_3$ 15,800
B: Polyoxyethylene octyl ether. Average molecular weight: 3,500

EXPERIMENTAL EXAMPLE 1

Test for mixing with plasma expander

For the clinical use as infusion fluid, the present emulsion is used preferably in combination with a plasma expander to replenish the deficiency in oncotic pressure. When the present emulsion was mixed with a plasma expander, the reversible precipitation which might be caused by interaction between both colloidal solutions was not detected, indicating that one of the difficulties which might be encountered in using the present emulsion as an infusion fluid has been eliminated.

The emulsions used in the experiment were perfluorodecalin-perfluoro-N,N-dibutylmethylamine (5:2) emulsions of various concentrations prepared in the same manner as in Example 3 [polyoxyethylenepolyoxypropylene copolymer, 3.4% (W/V); yolk phospholipids, 0.6% (W/V); potassium oleate, 0.04% (W/V)] and, as a reference, perfluorodecalin emulsions of various concentrations prepared according to Japanese Patent Application Kokai (Laid Open) No. 69219/75 corresponding to U.S. Pat. No. 3,962,439 [yolk phospholipid, 4% (W/V); potassium oleate, 0.02% (W/V)]. Each emulsion was made isotonic with the lactated Ringer's solution or Krebs-Ringer bicarbonate solution, then admixed with a plasma expander so that the final concentration of the latter may become 1 to 6% (W/V), and formation of precipitates was visually observed during 6 hrs. after mixing at room temperature. Plasma expanders used are hydroxyethylstarch (HES) (average molecular weight: 200,000 20% (W/V) in saline, supplied by Ajinomoto Co., Ltd.) and Dextran 40 [Dextran (average molecular weight, 40,000) 10% (W/V) in saline in water; supplied by The Green Cross Corp.].

The results are shown in Tables 2 and 3.

TABLE 2

| Final Dextran 40 content % (W/V) | Final fluorocarbon content, % (W/V) | Emulsion of the invention | | | Emulsion, Jap. Pat. Appl. Laid Open No. 69219/75 corresponding to U.S. Pat. No. 3,962,439 | | |
|---|---|---|---|---|---|---|---|
| | | 10% | 20% | 30% | 10% | 20% | 30% |
| 0.5 | | — | — | — | — | — | — |
| 1.0 | | — | — | — | — | — | + |
| 1.5 | | — | — | — | + | + | + |
| 2.0 | | — | — | — | + | + | + |
| 2.5 | | — | + | + | + | + | + |
| 3.0 | | + | + | + | + | + | + |

TABLE 3

| Final HES content, % (W/V) | Final fluorocarbon content % (W/V) | Emulsion of the invention | | | Emulsion, Jap. Pat. Appl. Laid Open No. 69219/75 corresponding to U.S. Pat. No. 3,962,439 | | |
|---|---|---|---|---|---|---|---|
| | | 10% | 20% | 30% | 10% | 20% | 30% |
| 1 | | — | — | — | — | — | — |
| 2 | | — | — | — | — | — | + |
| 3 | | — | — | — | — | + | + |
| 4 | | — | — | — | + | + | + |
| 5 | | — | + | + | + | + | + |
| 6 | | + | + | + | + | + | + |

Form the results obtained above, it was made clear that the present emulsion is much less affected by the presence of a plasma expander compared with the emulsion according to Japanese Patent Application Kokai (Laid Open) No. 69219/75, corresponding to U.S. Pat. No. 3,962,439 indicating that the present emulsion can be mixed with the Dextran 40 and HES preparation in any proporation to make it the physiologically colloidal isotonicity which obtained by addition of Dextran 40 and HES as a final concentration of 2% (W/V) and 3% (W/V), respectively.

Similar results to those mentioned above were also found in the emulsions prepared in Examples 1, 2, and 4.

EXPERIMENTAL EXAMPLE 2

In order to evaluate the efficacy of the present emulsion, the study on the exchange-transfusion in rats was done.

TABLE 4

| | | Ingredient | The present emulsion | Emulsion acc. to Jap. Pat. Appl. Open No. 69219/75 corresponding to U.S. Pat. No. 3,962,439 |
|---|---|---|---|---|
| Fluorocarbon emulsion (9 vol.) | Fluorocarbon | Perfluorodecalin | 25.3% (W/V) | 28% (W/V) |
| | | Perfluorodibutyl-monomethylamine | 9.8 | — |
| | | Pluronic F68* | 3.4 | — |
| | Surfactant | Yolk phospholipid | 0.6 | 4.0 |
| | | Potassium oleate | 0.004 | 0.02 |
| | | NaCl | 6.00 | 6.00 |
| | | NaHCO$_3$ | 2.1 | — |
| | | KCl | 0.336 | 0.336 |
| Electrolyte (1 vol.) | | Sodium lactate | — | 3.10 |
| | | MgCl$_2$ . 6H$_2$O | 0.427 | 0.427 |
| | | CaCl$_2$ . 2H$_2$O | 0.356 | — |
| | | D-glucose | 1.802 | 1.0 |

TABLE 4-continued

| Ingredient | The present emulsion | Emulsion acc. to Jap. Pat. Appl. Open No. 69219/75 corresponding to U.S. Pat. No. 3,962,439 |
|---|---|---|
| pH | 8.0 | 6.0 |

*Polyoxyethylene-polyoxypropylene copolymer (M.W. 8350)

Two kinds of fluorocarbon compound emulsion which were the present emulsion, the mixture of perfluorodecalin and perfluorodibutylmonomethylamine prepared in Example 3 and perfluorodecalin emulsion stabilized with yolk phospholipids according to Japanese Patent Application Kokai (Laid Open) No. 69219/75 corresponding to U.S. Pat. No. 3,962,439 were used in this experiment.

The ingredients of both emulsion were shown in Table 4.

To make the emulsion electrolyte and colloidal isotonification, one volume of hypertonic electrolytes solution shown Table 4 is added to 9 volume of the emulsion, and then, 1 volume of resultant emulsion containing electrolytes were mixed with 3 volume of 6% hydroxyethyl starch (molecular weight 40,000–50,000) in Ringer's lactated solution or rat plasma as reference, prior to use.

The rats (Wistar strain weighing 200 to 250 g) were exchange transfused with the emulsion containing electrolytes and hydroxyethyl starch or plasma by repeated bleeding from carotid artery and replacement transfusion through tail vein alternately up to hematocrit 1%, 4% and 7%, respectively, under the 100% oxygen atomosphere.

Then, the survival time of rats exchange-transfused were determined.

The results are shown in Table 5. As is evident in Table 5, the present emulsion was far more effective in saving the life of animal hemorraged massively in comparing with the perfluorodecalin emulsion stabilized with yolk phospholipids.

TABLE 5

| | Final hematocrit value % | Jointly with plasma | | Jointly with HES | |
|---|---|---|---|---|---|
| | | Survival time | | | |
| The present emulsion | 7 | >72$^{hours}$ | | >72$^{hours}$ | |
| | 4 | 50 | 00$^{min.}$ | >72 | |
| | 1 | 29 | 02 | 61 | 00$^{min.}$ |
| Emulsion acc. to Jap. Pat. Appl. Laid Open No. 69219/75 corresponding to U.S. Pat. No. 3,962,439 | 7 | 23$^{hours}$ | 10$^{min.}$ | 5$^{hours}$ | 53$^{min.}$ |
| | 4 | 11 | 5 | 5 | 2 |
| | 1 | 8 | 10 | 2 | 56 |

Note:
The values obtained from 5 rats in each group.

EXPERIMENTAL EXAMPLE 3

The present fluorocarbon compound emulsion obtained in Example 3 and the emulsion obtained according to Japanese Patent Application Kokai (Laid Open) No. 69219/75 corresponding to U.S. Pat. No. 3,962,439 were subjected to acute toxicity test.

In order to make these emulsion isotonification, one volume of electrolytes is added to 9 volume of the emulsion prior to use. The ingredients of these emulsions were shown in Table 4. As test animals were used wister strain male rats weighing 100 to 120 g. The rats were intravenously injected with the emulsion and the survival rate was observed during one week after injection. The results obtained are shown in Table 6. As seen in Table 6, the $LD_{50}$ of both emulsions was around 130 ml/kg body weight, indicating they were quite low-toxic.

TABLE 6

Acute toxicity of the fluorocarbon emulsion

| Sample | Dose ml/kg | Survival rate Number of survival rats Number of tested rats Days after injection | | | | | $LD_{50}$ (at 1 week) |
|---|---|---|---|---|---|---|---|
| | | 1 | 2 | 3 | 5 | 7 | |
| The present emulsion | 87 | 10/10 | 10/10 | 10/10 | 10/10 | 10/10 | 135 ml/kg |
| | 100 | 10/10 | 10/10 | 9/10 | 9/10 | 9/10 | |
| | 115 | 10/10 | 9/10 | 8/10 | 8/10 | 7/10 | |
| | 132 | 9/10 | 8/10 | 6/10 | 6/10 | 6/10 | |
| | 152 | 6/10 | 4/10 | 3/10 | 3/10 | 1/10 | |
| Emulsion acc. to Jap. Pat. Appl. Laid Open No. 69219/75 corresponding to U.S. Pat. No. 3,962,439 | 87 | 10/10 | 10/10 | 10/10 | 10/10 | 10/10 | 131 ml/kg |
| | 100 | 10/10 | 10/10 | 9/10 | 9/10 | 9/10 | |
| | 115 | 10/10 | 9/10 | 9/10 | 7/10 | 7/10 | |
| | 132 | 9/10 | 8/10 | 7/10 | 6/10 | 5/10 | |
| | 152 | 7/10 | 6/10 | 4/10 | 3/10 | 1/10 | |

EXPERIMENTAL EXAMPLE 4

In order to examine hemolytic effect of the fluorocarbon preparations in the extracorporeal circulation system, experiments in vitro were carried out by using red blood cells of rabbit.

Two emulsion preparations used in Experimental Example 2 as shown in Table 4 were admixed with a lactated Ringer's solution so as to become substantially isotonic physiologically. The resulting isotonic emulsion preparations were mixed with the heperinized rabbit blood in a ratio of 3:1, 1:1, and 1:3 to prepare sample solutions for the tests. The hemolytic effect was evaluated by measuring the free hemoglobin content of 8 ml of the blood after having been kept at 37° C. for 6 hours. Determination of hemolyzed hemoglobin was determined by the cyanomethemoglobin method (Kampen, E. J. and Ziilstram, W. J. Clin. Chim. Acta. 6, 538, 1961).

The results obtained are shown in Table 7.

TABLE 7

|  | Free hemoglobin, mg | | |
| --- | --- | --- | --- |
| Fluorocarbon : blood ratio | 1:3 | 1:1 | 3:1 |
| Emulsion of this invention | 36 | 81 | 180 |
| Emulsion acc. to Jap. Pat. Appl. Laid Open No. 69219/75 corresponding to U.S. Pat. No. 3,962,439 | 298.5 | >4,000 | 3,380 |
| Lactated Ringer's solution (reference) | 36 | 128 | 141 |

As seen from Table 7, the hemolytic effect of the present emulsion is far smaller than that of prior art and not much different from that of the lactated Ringer's solution used as reference.

What is claimed is:

1. A stable emulsion in a physiologically acceptable aqueous medium of an oxygen-transferrable perfluorocarbon compound having a particle size of about 0.05 to 0.3μ, which comprises 10 to 50% (w/v) in the sum of the amount of (A) perfluorodecalin and (B) perfluoro tripropylamine; 2.0 to 5.0% (w/v) in the amount of a high molecular weight nonionic surfactant which is a polyoxyethylene-polyoxypropylene copolymer having a molecular weight of 2,000 to 20,000; 0.1 to 1.0% (w/v) in the amount of a phospholipid; and 0.004 to 0.1% (w/v) in the amount of at least one fatty acid compound selected from the group consisting of fatty acids having 8 to 22 carbon atoms, physiologically acceptable salts and monoglycerides thereof; the proportion of the said perfluorocarbon compound (A) and the said perfluoro tert-amine (B) being 95–50 to 5–50 by weight.

2. The emulsion according to claim 1, wherein the physiologically acceptable aqueous medium is water or isotonic solution.

3. The emulsion according to claim 2, wherein the isotonic solution is a lactated Ringer's solution or a Ringer's solution containing glucose.

4. The emulsion according to claim 1, wherein the fatty acid compound is caprylic acid, capric acid, lauric acid, myristic acid, palmitic acid, stearic acid, behenic acid, palmitoleic acid, oleic acid, linoleic acid or arachidonic acid.

5. The emulsion according to claim 1, wherein the fatty acid compound is an alkali metal salt of a fatty acid selected from caprylic acid, capric acid, lauric acid, myristic acid, palmitic acid, stearic acid, behenic acid, palmitoleic acid, oleic acid, linoleic acid and arachidonic acid.

6. The emulsion according to claim 5, wherein the alkali metal salt of the fatty acid is potassium oleate or sodium oleate.

7. The emulsion according to claim 5, wherein the alkali metal salt of the fatty acid is potassium palmitate or sodium palmitate.

8. The emulsion according to claim 1, wherein the fatty acid compound is monoglyceride of a fatty acid selected from caprylic acid, capric acid, lauric acid, myristic acid, palmitic acid, stearic acid, behenic acid, palmitoleic acid, oleic acid, linoleic acid and arachidonic acid.

9. The emulsion according to claim 1, wherein the phospholipid is egg yolk phospholipids or soybean phospholipids.

10. The emulsion according to claim 1, wherein the emulsion is made isotonicity in its onocotic pressure with blood by the addition of plasma or plasma expander.

11. The emulsion according to claim 30, wherein the plasma expander is hydroxyethyl starch or modified gelatin or dextran.

12. The emulsion according to claim 1, wherein the polyoxyethylene-polyoxypropylene copolymer has a molecular weight of 8,350 to 15,800.

13. The emulsion according to claim 12, wherein the fatty acid compound is potassium oleate and the plasma expander is hydroxyethyl starch.

14. The emulsion of claim 12 wherein the phospholipid is egg yolk phospholipids, and the fatty acid component is oleic acid, sodium oleate or potassium oleate.

15. The emulsion of claim 14 wherein the physiologically acceptable aqueous medium is an isotonic solution and contains hydroxyethyl starch, modified gelatin or dextran as a plasma expander.

16. The emulsion of claim 14 wherein the phospholipid is egg yolk phospholipids or soybean phospholipids.

17. The emulsion of claim 1 wherein the proportion of perfluorodecalin to perfluoro tripropylamine is from 64 to 25 to 50 to 50 by weight.

18. The emulsion of claim 1 wherein the polyethylene-polyoxypropylene copolymer has a molecular weight of 8,350 to 15,800, the fatty acid compound is potassium oleate, there is present hydroxyethyl starch as a plasma extender in an amount of 1 to 5% (w/v) and the phospholipid is egg yolk phospholipids or soybean phospholipids.

19. The emulsion of claim 18 wherein the polyoxyethylene-polyoxypropylene copolymer has a molecular weight of 8,350, the hydroxyethyl starch is present in an amount of 3%, the physiologically acceptable aqueous medium is a Ringer's solution containing glucose, the total concentration of the polyoxyethylene-polypropylene copolymer, the phospholipid and potassium oleate is 3.0 to 3.5% (w/v) of which about 0.4 to about 0.6% (w/v) is phospholipid, 0.004 to 0.1% (w/v) is potassium oleate and the balance is the polyoxyethylene-polyoxypropylene copolymer.

20. The emulsion of claim 19 wherein the phospholipid is egg yolk phospholipids.

* * * * *